(12) United States Patent
Liang

(10) Patent No.: US 11,058,618 B1
(45) Date of Patent: Jul. 13, 2021

(54) HAIR TREATMENT COMPOSITIONS

(71) Applicant: L'OREAL, Paris (FR)

(72) Inventor: Jun Liang, Staten Island, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/863,294

(22) Filed: Apr. 30, 2020

(51) Int. Cl.
| | | |
|---|---|---|
| *A61Q 5/02* | (2006.01) | |
| *A61Q 5/06* | (2006.01) | |
| *A61Q 5/12* | (2006.01) | |
| *A61K 8/34* | (2006.01) | |
| *A61Q 5/00* | (2006.01) | |
| *A61K 8/36* | (2006.01) | |
| *A61K 8/44* | (2006.01) | |
| *A61K 8/41* | (2006.01) | |

(52) U.S. Cl.
CPC .............. *A61K 8/345* (2013.01); *A61K 8/342* (2013.01); *A61K 8/361* (2013.01); *A61K 8/41* (2013.01); *A61K 8/44* (2013.01); *A61Q 5/002* (2013.01); *A61Q 5/02* (2013.01); *A61Q 5/06* (2013.01); *A61Q 5/12* (2013.01); *A61K 2800/31* (2013.01); *A61K 2800/48* (2013.01)

(58) Field of Classification Search
None
See application file for complete search history.

(56) References Cited

U.S. PATENT DOCUMENTS

| | | |
|---|---|---|
| 7,041,142 B2 | 5/2006 | Chan et al. |
| 8,486,425 B1 | 7/2013 | Shah et al. |
| 10,004,673 B1 | 6/2018 | Elsen-Wahrer et al. |
| 2008/0311067 A1* | 12/2008 | Murray ............ A61K 8/42 424/70.27 |
| 2011/0165110 A1 | 7/2011 | Kinoshita et al. |
| 2013/0330291 A1* | 12/2013 | Hoffmann ............ A61Q 5/12 424/70.12 |
| 2016/0206533 A1* | 7/2016 | Callens ............ A61Q 5/12 |
| 2016/0235651 A1 | 8/2016 | Decoster et al. |
| 2017/0312206 A1* | 11/2017 | Davis ............ A61Q 7/00 |
| 2019/0365628 A1 | 12/2019 | Koide et al. |

FOREIGN PATENT DOCUMENTS

WO WO-2018/178341 A1 10/2018

OTHER PUBLICATIONS

Preliminary Search Report and Written Opinion dated Mar. 19, 2021 in corresponding French Application No. 2006369.

* cited by examiner

*Primary Examiner* — Jyothsna A Venkat
(74) *Attorney, Agent, or Firm* — Polsinelli PC

(57) ABSTRACT

The hair treatment compositions of the instant disclosure typically include about 20 wt. % or more of a polyol; about 5 wt. % to about 50 wt. % of a monoalcohol having a carbon chain of 1 to 10 carbons; about 0.1 to about 5 wt. % of a fatty acid; about 0.1 to about 15 wt. % of a fatty amine; about 0.1 to about 15 wt. % of a fatty alcohol; and about 0.1 to about 15 wt. % of an emollient, wherein all weight percentages are based on the total weight of the hair treatment composition. The hair treatment composition typically has a weight ratio of the amount of polyol to the amount the monoalcohol of 20:1 to 1:1. Additionally, the hair treatment may have a molar ratio of the amount of the fatty acid to the amount of the fatty amine of 0.8:1 to 1.2:1.

11 Claims, 1 Drawing Sheet

| | Exemplary Composition A | Comparative Composition F |
|---|---|---|
| Bright Field (20x) | 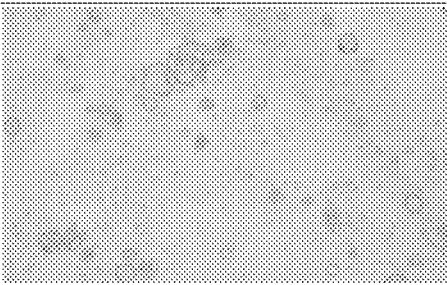 | 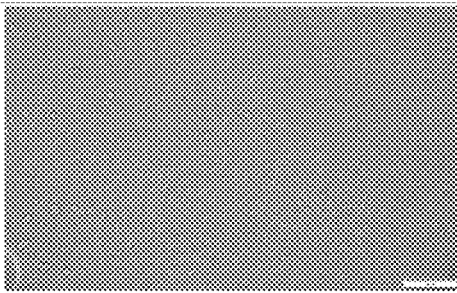 |
| Polarized (20x) | 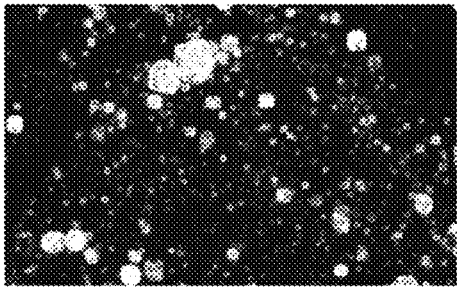 | 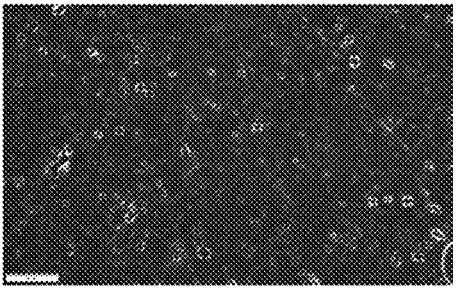 |

HAIR TREATMENT COMPOSITIONS

FIELD OF THE DISCLOSURE

The instant disclosure is directed to hair treatment compositions and, particularly, hair treatment compositions having a unique combination and ratio of fatty acids to fatty amines. Aspects of the instant disclosure also relate to methods for making and using such hair treatment compositions.

BACKGROUND OF THE DISCLOSURE

Many individuals suffer from dry and damaged hair. Dryness and damage can occur due to several factors including weather exposure, mechanical treatments (e.g. brushing hair), excessive treatments using chemicals, dying hair, heat styling, etc. In combination, using cleansing products that can be excessively stripping of hair's natural oils, can also lead to split ends, dull hair, and exacerbate dry hair. To mitigate the damage, many individuals utilize conditioners or other hair treatments for mitigating the damage and improve the health of hair.

Conditioners are typically emulsions having a dispersed oil phase and a continuous aqueous phase. As a result of logistic systems, cosmetic products must be formulated to withstand both high temperatures and low temperatures associated with transportation (e.g., in back of a truck) from the manufacturing plant to the warehouse storage to the retail stores and, ultimately, to the consumer. Accordingly, conditioners are typically formulated to maintain a stable emulsion over large temperature ranges as well as repeated temperature swings.

There is an ongoing need for new and improved formulations that offer consumers a unique sensorial experience. This unique sensorial experience may be related to product performance and/or product texture and consistency and/or tactile experience.

SUMMARY OF THE DISCLOSURE

The instant disclosure relates hair treatment compositions and, particularly, hair treatment compositions having a unique combination and ratio of fatty acids, fatty amines, and fatty alcohols, and particularly a unique ratio of fatty acids to fatty amines. The hair treatment compositions provide unique sensorial experiences and provide improved hair properties, including, e.g., smoothness, lightness or weightless feel, and shine.

The hair treatment compositions of the instant disclosure typically include:
(a) about 20 wt. % or more of a polyol;
(b) about 5 wt. % to about 50 wt. % of a monoalcohol having a carbon chain of 1 to 10 carbons,
    wherein a weight ratio of the amount of polyol of (a) to the amount of the monoalcohol of (b) is 20:1 to 1:1;
(c) about 0.1 to about 5 wt. % of a fatty acid;
(d) about 0.1 to about 15 wt. % of a fatty amine,
    wherein a molar ratio of the amount of the fatty acid of (c) to the amount of the fatty amine of (d) is 0.8:1 to 1.2:1;
(e) about 0.1 to about 15 wt. % of a fatty alcohol; and
(f) about 0.1 to about 15 wt. % of an emollient,
    wherein all weight percentages are based on the total weight of the hair treatment composition.

Preferably, hair treatment compositions are formulated to have a weight ratio of the amount of polyol of (a) to the amount of the monoalcohol of (b) that is 10:1 to 1:1. In some instances, the weight ratio of the amount of polyol of (a) to the amount of the monoalcohol of (b) is 5:1 to 1:1.

The polyol may be glycerin or a glycol, such as those chosen from ethylene glycol, propylene glycol, butylene glycol, hexylene glycol, pentylene glycol, diethylene glycol, dipropylene glycol, 1,3 propanediol, polyethylene glycols, and a mixture thereof.

The fatty acid typically has a carbon chain of 12 to 18 carbons. Suitable fatty acid(s) include those chosen from lauric acid, myristic acid, palmitic acid, stearic acid, or a mixture thereof. The fatty amine is preferably a primary alkylamine, a second alkylamine, a tertiary alkylamine, an alkylamidoamines, or a mixture thereof. In at least one preferable instance, the carbon chain of the fatty amine has a length that is within 4 carbon atoms of the length of the carbon chain of the fatty acid. The hair treatment compositions may have a molar ratio of the amount of the fatty acid of (c) to the amount of the fatty amine of (d) that is 0.85:1 to 1.15:1. In at least one case, the molar ratio of the amount of the fatty acid of (c) to the amount of the fatty amine of (d) is 0.9:1 to 1.1:1.

Additionally or alternatively, the hair treatment compositions may also have a viscosity of about 1 Pa·s or less at a shear rate of $1 \text{ s}^{-1}$. In some instances, the hair treatment compositions are free of water. In further instances, the hair treatment compositions are free of thickening agents and/or silicones. The hair treatment composition may have a fatty alcohol that has a carbon chain of 12 to 18 carbons.

Aspects of the instant disclosure also relate to methods for making and using such hair treatment compositions. A method for cleaning hair according to aspects of the disclosure typically includes:
(I) applying a hair treatment composition comprising:
   (a) about 20 wt. % or more of a polyol;
   (b) about 5 to about 50 wt. % of a monoalcohol having a carbon chain of 1 to 10 carbons, wherein a weight ratio of the amount of glycol of (a) to the amount of the monoalcohol of (b) is 20:1 to 1:1;
   (c) about 0.1 to about 5 wt. % of a fatty acid;
   (d) about 0.1 to about 15 wt. % of a fatty amine, wherein a molar ratio of the amount of the fatty acid of (c) to the amount of the fatty amine of (d) is 0.8:1 to 1.2:1;
   (e) about 0.1 to about 15 wt. % of a fatty alcohol; and
   (f) about 0.1 to about 15 wt. % of an emollient,
       wherein all weight percentages are based on the total weight of the hair treatment composition.
(II) rinsing the hair cleansing composition from the hair.

The method for cleaning hair may condition the hair; provide curl definition to the hair; provide frizz control to the hair; improve ease of combability and detangling; protect the hair from damage; and/or increase the appearance of the hair volume.

Additionally or alternatively, the method may include one or more of the following steps:
  mixing with a shampoo prior to application to hair;
  layering onto hair with a shampoo;
  applying to hair after a shampoo has been rinsed from the hair;
  layering onto hair with a conditioner;
  mixing with a conditioner prior to application to hair;
  applying to hair after a conditioner has been rinsed from the hair;
  mixing with a leave-in hair treatment prior to application to hair;

mixing with a mask composition prior to application to hair; or applying to hair after a mask composition has been applied to and optionally, rinsed from the hair.

BRIEF DESCRIPTION OF THE DRAWING

Implementation of the present technology will now be described, by way of example only, with reference to the attached FIGURE, wherein:

FIGURE includes images from a microscope of a mixed structure and a lamellar phase of an exemplary hair treatment composition and a comparative composition, respectively, in accordance with aspects of the disclosure.

It should be understood that the various aspects are not limited to the arrangements and instrumentality shown in the drawings.

DETAILED DESCRIPTION OF THE DISCLOSURE

The instant disclosure relates to hair treatment compositions and, particularly, hair treatment compositions having a unique combination and ratio of fatty acid to fatty amine. Upon application to wet or damp hair, the hair treatment compositions may form a mixture structure of a lamellar phase having vesicles and/or crystals. Advantageously, the hair treatment compositions may provide enhanced deposition of fatty acids and fatty amines. The inventors discovered that the unique combination and ratio of fatty acids and fatty amines of the hair treatment compositions provide enhanced smoothness, lightness, shine, and other attributes to hair.

The hair treatment compositions of the instant disclosure typically include:
  (a) about 20 wt. % or more of a polyol;
  (b) about 5 wt. % to about 50 wt. % of a monoalcohol having a carbon chain of 1 to 10 carbons,
    wherein a weight ratio of the amount of polyol of (a) to the amount of the monoalcohol of (b) is 20:1 to 1:1;
  (c) about 0.1 to about 5 wt. % of a fatty acid;
  (d) about 0.1 to about 15 wt. % of a fatty amine,
    wherein a molar ratio of the amount of the fatty acid of (c) to the amount of the fatty amine of (d) is 0.8:1 to 1.2:1;
  (e) about 0.1 to about 15 wt. % of a fatty alcohol; and
  (f) about 0.1 to about 15 wt. % of an emollient,
    wherein all weight percentages are based on the total weight of the hair treatment composition.

During use, a user combines the hair treatment compositions with extraneous water (e.g., water other than the water already included in the hair treatment composition). As the hair treatment composition becomes mixed with extraneous water, the hair treatment composition may form lamellar structure having crystals. As used herein, the term "mixed structure" refers to a combination of a lamellar phase and crystals. A "lamellar phase" refers generally to packing of polar-headed long chain nonpolar-tail molecules in an environment of bulk polar liquid (i.e., water from the hair), as sheets of bilayers separated by bulk liquid. Without being limited to any specific theory, the inventors believe that the unique combination and ratio of fatty acid(s), fatty amine(s), and fatty alcohol(s) contribute to the production of the mixed structure. Additionally or alternatively, the hair treatment composition may form an opaque emulsion when combined with extraneous water.

The hair treatment composition may form a mixed structure upon combination with extraneous water, for example, from a user's wet or damp hands, wet or damp hair, and/or from the faucet and the like. This can occur, for example, when a consumer applies the hair treatment composition to a wet or damp part of the body (e.g., hands, face, skin, hair, etc.). The user may then physically manipulate the applied hair treatment composition (for example, by rubbing the hands together or rubbing the composition against another part of the body such as the face, hair, etc.). The mixed structure may be formed by combining extraneous water with the hair treatment composition in an ratio (water: composition) ranging from 0.1:1 to 3:1, preferably 0.5:1 or 1:1 or 1.5:1 or 2:1. Additionally and/or alternatively, the mixed structure may be formed by combining extraneous water in an amount such that the total amount of water in the hair treatment composition increases to more than 10 wt. % or, in some instances, to 12 wt. % or more, 15 wt. % or more, 20 wt. % or more, 25 wt. % or more, or 30 wt. % or more, based on the total weight of the hair treatment composition before combination with extraneous water.

The mixed structure formed from the combination of the hair treatment composition and extraneous water may occur without active mixing from a user or in conjunction with active mixing from the user. For example, in some instances, the mixed structure is formed automatically without the need for mixing. In other words, the hair treatment composition becomes sufficiently combined with extraneous water to form the mixed structure by simply coming into contact with extraneous water. In some instances, however, a minimal amount of mixing may be needed, and may be encouraged, to more thoroughly form the mixed structure. This can easily be achieved during use of the hair treatment composition, for example, by physically manipulating (e.g., mixing) the hair treatment composition with extraneous water using the body (e.g., with the hands).

The hair treatment composition is typically translucent or clear before combination with extraneous water. For example, the hair treatment composition may have a transmittance of at least 50% at a wavelength of 600 nm, for example measured using a Lambda 40 UV-visible spectrometer. In some instances, the compositions may have a transmittance of at least 60%, at least 70%, at least 80%, at least 90%, or at least 95% at a wavelength of 600 nm, measured, for example, using a Lambda 40 UV-visible spectrometer.

Preferably, the hair treatment composition may be formulated to have an amount of polyol to an amount of monoalcohols in a weight ratio (i.e. total polyols:total monoalcohols) of 20:1 to 1:1. For example, the weight ratio of the amount of polyols to the amount of monoalcohols may be from 18:1 to 1:1, 15:1 to 1:1, 10:1 to 1:1, 7:1 to 1:1, 6:1 to 1:1, 5:1 to 1:1, or 4:1 to 1.1:1, including ranges and sub-ranges therebetween. In at least one embodiment, the hair treatment composition is formulated such that the total amount of polyols is greater than the total amount of monoalcohols.

Additionally or alternatively, the hair treatment compositions may be formulated to have a molar ratio of the amount of fatty acid to the amount of fatty amine of 0.8:1 to 1.2:1. For example, the molar ratio of fatty acid to fatty amine may be 0.8:1 to 1.2:1, 0.85:1 to 1.2:1, 0.9:1 to 1.2:1, 0.95:1 to 1.2:1, 0.8:1 to 1.15:1, 0.8:1 to 1.1:1, 0.8:1 to 1.05:1, including ranges and sub-ranges therebetween. In some instances, the hair treatment composition is formulated to have a molar ratio of fatty acid to fatty amine of 0.85:1 to 1.15:1, 0.9:1 to 1.1:1, or 0.95:1 to 1.05:1. The hair treatment composition may have a crystallization temperature that is 20° C. or less before addition of extraneous water. Surprisingly, the inventors discover that the hair treatment composition can be formulated to have a ratio of fatty acid to fatty amine that promotes a lowered recrystallization temperature of 20° C. or less before addition of extraneous water.

The hair treatment composition may be formulated such that the carbon chain of the fatty amine has a length that is within 4 carbon atoms of the length of the carbon chain of the fatty acid. In other words, the fatty amine and the fatty acid may be chosen such that the length of the carbon chain of the fatty amine is not greater than the length of the carbon chain of the fatty acid by 4 carbon atoms and also is not less than the length of the carbon chain of the same fatty acid by 4 carbon atoms. In some instances, the length of the carbon chain of the fatty amine and the length of the carbon chain of the fatty acid are not greater than the length of the carbon chain of the fatty alcohol by 6 carbon atoms and also are not less than the length of the carbon chain of the same fatty alcohol by 6 carbon atoms. In other instances, the length of the carbon chain of the fatty amine and the length of the carbon chain of the fatty acid are not greater than the length of the carbon chain of the fatty alcohol by 4 carbon atoms and also are not less than the length of the carbon chain of the same fatty alcohol by 4 carbon atoms.

The hair treatment compositions typically have a viscosity of about 1 Pa·s or less at a shear rate of 1 s$^{-1}$ at a temperature of 25° C. before combination with extraneous water. For example, the hair treatment compositions may have a viscosity of about 1 mPa·s to about 1 Pa·s, about 1 mPa·s to about 800 mPa·s, about 1 mPa·s to about 600 mPa·s, about 1 mPa·s to about 500 mPa·s, about 1 mPa·s to about 400 mPa·s, or about 1 mPa·s to about 300 mPa·s; about 100 mPa·s to about 1 Pa·s, about 100 mPa·s to about 800 mPa·s, about 100 mPa·s to about 600 mPa·s, about 100 mPa·s to about 500 mPa·s, about 100 mPa·s to about 400 mPa·s, or about 100 mPa·s to about 300 mPa·s; about 300 mPa·s to about 1 Pa·s, about 300 mPa·s to about 800 mPa·s, about 300 mPa·s to about 600 mPa·s, or about 300 mPa·s to about 500 mPa·s; about 500 mPa·s to about 1 Pa·s, about 500 mPa·s to about 800 mPa·s, or about 500 mPa·s to about 600 mPa·s, including ranges and subranges therebetween, at a temperature of 25° C. before combination with extraneous water. The viscosity measurements can be carried out, for example, using a Brookfield viscometer, Model RVT (Brookfield Engineering Laboratories, Inc.) at about 60 revolutions per minute (RPM), at ambient room temperature of about 20 to 25° C.; spindle sizes may be selected in accordance with the standard operating recommendations form the manufacturer, ranging from disk spindle No. 1 to No. 4.

In some instances, the hair treatment composition is free or substantially free of water (anhydrous or substantially anhydrous). Alternatively or additionally, the hair treatment composition may have an amount of water that is less than 6 wt. %, preferably less than 5 wt. %, preferably less than 4 wt. %, preferably less than 3 wt. %, preferably less than 2 wt. %, preferably less than 1 wt. %, and/or less than 0.5 wt. %, based on the total weight of the hair treatment composition. In at least embodiment, the hair treatment composition has substantially/essentially 0 wt. % or 0 wt. % of water, based on the total weight of the hair treatment composition.

In some instances, the hair treatment composition is free or substantially free of silicone. In some instances, the hair treatment composition may have an amount of silicone that is less than 6 wt. %, preferably less than 5 wt. %, preferably less than 4 wt. %, preferably less than 3 wt. %, preferably less than 2 wt. %, preferably less than 1 wt. %, preferably less than 0.5 wt. %, and/or preferably less than 0.1 wt. %, based on the total weight of the hair treatment composition. In at least embodiment, the hair treatment composition has substantially/essentially 0 wt. % or 0 wt. % of silicone, based on the total weight of the hair treatment composition.

The hair treatment composition may be free of or substantially free of polyurethane resin. In some cases, the hair treatment composition may have an amount of polyurethane resin that is less than 6 wt. %, preferably less than 5 wt. %, preferably less than 4 wt. %, preferably less than 3 wt. %, preferably less than 2 wt. %, preferably less than 1 wt. %, preferably less than 0.5 wt. %, and/or preferably less than 0.1 wt. %, based on the total weight of the hair treatment composition. In at least embodiment, the hair treatment composition has substantially/essentially 0 wt. % or 0 wt. % of polyurethane resin, based on the total weight of the hair treatment composition.

Suitable components, such as those listed below, may be included or excluded from the formulations for the hair treatment compositions depending on the specific combination of other components, the form of the hair treatment compositions, and/or the use of the formulation (e.g., a lotion, gel, cream, spray, etc.).

Polyol(s)

The hair treatment compositions include one or more polyols, e.g., such as those chosen from ethylene glycol, propylene glycol, butylene glycol, hexylene glycol, pentylene glycol, diethylene glycol, dipropylene glycol, 1,3 propanediol, 1,4-butanediol, 1,5-pentanediol, hexane-1,6-diol, glycerin, diglycerin, and a mixture thereof. The amount of polyol(s) present in the hair treatment composition typically ranges from about 20 wt. % or more, based on the total weight of the hair treatment composition. For example, the amount of polyol(s) in the hair treatment composition may be about 20 to about 87 wt. %, about 20 to about 85 wt. %, about 20 to about 80 wt. %, about 20 to about 75 wt. %, about 20 to about 70 wt. %, about 20 to about 65 wt. %, about 20 to about 60 wt. %, about 20 to about 55 wt. %, about 20 to about 50 wt. %, about 20 to about 45 wt. %, about 20 to about 40 wt. %, about 20 to about 35 wt. %, about 20 to about 30 wt. %; about 30 to about 87 wt. %, about 30 to about 85 wt. %, about 30 to about 80 wt. %, about 30 to about 75 wt. %, about 30 to about 70 wt. %, about 30 to about 65 wt. %, about 30 to about 60 wt. %, about 30 to about 55 wt. %, about 30 to about 50 wt. %, about 30 to about 45 wt. %, about 30 to about 40 wt. %; about 40 to about 87 wt. %, about 40 to about 85 wt. %, about 40 to about 80 wt. %, about 40 to about 75 wt. %, about 40 to about 70 wt. %, about 40 to about 65 wt. %, about 40 to about 60 wt. %, about 40 to about 55 wt. %, about 40 to about 50 wt. %; about 50 to about 87 wt. %, about 50 to about 85 wt. %, about 50 to about 80 wt. %, about 50 to about 75 wt. %, about 50 to about 70 wt. %, about 50 to about 65 wt. %, about 50 to about 60 wt. %; about 60 to about 87 wt. %, about 60 to about 85 wt. %, about 60 to about 80 wt. %, about 60 to about 75 wt. %, about 60 to about 70 wt. %; about 65 to about 87 wt. %, about 65 to about 85 wt. %, about 65 to about 80 wt. %, about 65 to about 75 wt. %; about 70 to about 87 wt. %, about 70 to about 85 wt. %, about 70 to about 75 wt. %, including all ranges and sub-ranges therebetween, based on the total weight of the hair treatment composition.

The term "polyol" should be understood as meaning, within the meaning of the present disclosure, an organic molecule comprising at least two free hydroxyl groups. The polyols of the hair treatment composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the hair treatment composition, in certain instances, include ethylene glycol, propylene glycol, butylene glycol, hexylene glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the hair treatment composition comprises at least propylene glycol, and optionally one or more polyols other than propylene glycol.

Non-limiting examples of polyols that may, optionally, be included in the hair treatment include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

Monoalcohol(s)

The hair treatment compositions include monoalcohol(s), such as those having 1 to 10 carbons, preferably, from 2 to 6 carbons. The amount of monoalcohol present in the hair treatment composition may range from about 5 to about 50 wt. %, based on the total weight of the hair treatment composition. For example, the hair treatment composition may have monoalcohol in an amount of about 5 to about 50 wt. %, about 5 to about 45 wt. %, about 5 to about 40 wt. %, about 5 to about 35 wt. %, about 5 to about 30 wt. %, about 5 to about 25 wt. %; about 10 to about 50 wt. %, about 10 to about 45 wt. %, about 10 to about 40 wt. %, about 10 to about 35 wt. %, about 10 to about 30 wt. %, about 10 to about 25 wt. %; about 15 to about 50 wt. %, about 15 to about 45 wt. %, about 15 to about 40 wt. %, about 15 to about 35 wt. %, about 15 to about 30 wt. %, or about 15 to about 25 wt. % including all ranges and sub-ranges therebetween, based on the total weight of the hair treatment composition.

The one or more monoalcohols of the hair treatment composition may be chosen from ethanol, propanol, butanol, pentanol, hexanol, isopropyl alcohol, cyclohexanol, isobutyl alcohol, 2-methyl-2-butanol (2-methylbutan-2-ol), and a mixture thereof. In some instances, the monoalcohols comprise or are chosen from ethanol, propanol, butanol, pentanol, an isomer thereof, or a combination thereof. In further instances, the one or more monoalcohol(s) includes or consists of ethanol.

The hair treatment composition may be formulated to have an amount of glycol to an amount of monoalcohols in a ratio (i.e. total glycols:total monoalcohols) of 20:1 to 1:1. For example, the weight ratio of the amount of polyols to the amount of monoalcohols may be from 18:1 to 1:1, 15:1 to 1:1, 10:1 to 1:1, 7:1 to 1:1, 6:1 to 1:1, 5:1 to 1:1, or 4:1 to 1.1:1, including ranges and sub-ranges therebetween. In at least one embodiment, the hair treatment composition is formulated such that the total amount of polyols is greater than the total amount of monoalcohols. In at least another instance, the hair treatment composition is formulated such that the total amount of glycol is greater than the total amount of monoalcohols.

Fatty Acid(s)

The hair treatment composition includes fatty acids in an amount that may vary, but typically ranges from about 0.1 to about 5 wt. %, based on the total weight of the hair treatment composition. For example, the amount of fatty acids(s) present in the hair treatment composition may range from about 0.1 to about 5 wt. %, about 0.1 to about 4 wt. %, about 0.1 to about 3 wt. %, about 0.1 to about 2 wt. %; about 0.2 to about 1 wt. %, about 0.5 to about 5 wt. %, about 0.5 to about 4 wt. %, about 0.5 to about 3 wt. %, about 0.5 to about 2 wt. %, about 0.7 to about 5 wt. %, about 0.7 to about 4 wt. %, about 0.7 to about 3 wt. %, about 0.7 to about 2 wt. %; about 1 to about 5 wt. %, about 1 to about 4 wt. %, or about 1 to about 3 wt. %, about 1 to about 2 wt. %, including all ranges and sub-ranges therebetween, based on the total weight of the hair treatment composition.

The fatty acids may be straight or branched chain acids and/or may be saturated or unsaturated. The fatty acid may have 8 to 30 carbons, e.g., 8 to 25, 8 to 22, 8 to 20, 8 to 18, or 8 to 16 carbons. In some cases, the fatty acid has 12 to 30, 12 to 25, 12 to 22, 12 to 20, 12 to 18 carbons. In further cases, the fatty acids may comprise $C_8$-$C_{22}$ or $C_{14}$-$C_{22}$ fatty groups, which may be saturated or unsaturated linear alkyl chain containing. The fatty acids may have fatty groups chosen from stearate, isostearate, linoleate, oleate, behenate, arachidonate, palmitate, myristate, laurate, caprate, isostearyl, stearyl, linoleyl, oleyl, behenyl, myristyl, lauryl or capryl chains, and mixtures thereof.

Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. The fatty acids may be selected from the group consisting of palmitic acid, myristic acid, stearic acid, and a mixture thereof. In some instances, the fatty acid may be chosen from fatty acids, fatty acid derivatives and/or alkoxylated fatty acids.

Non-limiting examples of polyglycerol esters of fatty acids include those of the following formula:

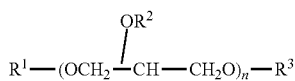

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Non-limiting examples fatty acid alkanolamides include fatty acid monoalkanolamides, fatty acid dialkanolamides, or fatty acid isoalkanolamides. Fatty acid alkanolamides may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Fatty Amine(s)

The hair treatment composition includes fatty amine(s) in an amount that may vary, but typically ranges from about 0.1 to about 15 wt. %, based on the total weight of the hair treatment composition. For example, the amount of fatty amine(s) present in the hair treatment composition may range from about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %; about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %; about 0.5 to about 1.5 wt. %, about 0.7 to about 15 wt. %, about 0.7 to about 10 wt. %, about 0.7 to about 8 wt. %, about 0.7 to about 6 wt. %, about 0.7 to about 5 wt. %, about 0.7 to about 4 wt. %, about 0.7 to about 3 wt. %, about 0.7 to about 2 wt. %; about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %; about 1.5 to about 15 wt. %, about 1.5 to about 10 wt. %, about 1.5 to about 8 wt. %, about 1.5 to about 6 wt. %, about 1.5 to about 5 wt. %, about 1.5 to about 4 wt. %, including all ranges and sub-ranges therebetween, based on the total weight of the hair treatment composition.

The fatty amine may contain at least one alkyl group (e.g., alkyl, alkyl ester, alkyl ether or alky amide) that has an average carbon chain length of 12 or greater, preferably 12 to 22 carbon atoms. Suitable fatty amines include $C_{12}$-$C_{22}$ alkyl or alkoxy amines; and $C_{12}$-$C_{22}$ alkyl or alkoxy amido amines. The amines can be monoamines, diamines, triamines or polyamines. The amino group can be primary, secondary, tertiary or quaternary. In some instances, the fatty amine comprises or is chosen from a quaternary ammonium, an alkylamines, an alkylamidoamines, or a mixture thereof. In further instances the fatty amine is an amine oxides such as ($C_{10}$-$C_{14}$)alkylamine.

The one or more alkylamines and/or one or more alkanolamines that may be included in the compositions include compounds of the following formula:

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some cases, $R_3$, $R_4$ and $R_5$ are independently H, $C_1$-$C_2$ alkyl, $C_1$-$C_{20}$ monohydroxyalkyl or $C_2$-$C_{20}$ polyhydroxyalkyl, provided that at least one of $R_3$, $R_4$ and $R_5$ is an alkyl or mono or polyhydroxyalkyl. Finally, $R_3$, $R_4$ and $R_5$ may independently be H, $C_1$-$C_{10}$alkyl, $C_1$-$C_{10}$ monohydroxyalkyl or $C_2$-$C_{10}$ polyhydroxyalkyl, provided that at least one of $R_3$, $R_4$ and $R_5$ is an alkyl or mono or polyhydroxyalkyl.

Non-limiting examples of alkylamines include methylamine, ethylamine, butylamine, octylamine, decylamine, dodecylamine, stearylamine, naphthylamine, benzylamine, aniline, cyclohexylamine, and mixtures thereof.

Non-limiting examples of alkanolamines include monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

Further non-limiting examples of alkylamines include aliphatic amine compounds corresponding to the following formula and their salts:

wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. In some cases, the groups R', which may be identical or different, are H or a methyl group.

Fatty amines that may be mentioned include but are not limited to alkylamidoamines, for instance ($C_8$-$C_{30}$)alkylamidodi($C_1$-$C_6$)alkylamines, and ($C_8$-$C_{30}$)alkylamido($C_1$-$C_6$) dialkylamines, such as stearamidopropyldimethylamine (MACKINE 301 sold by MacIntyre).

Suitable amines for use in the hair treatment compositions may be tertiary and quaternary fatty amines. One group of useful tertiary amines incorporating a single carbon chain of about 12 to about 22 carbon atoms (ester, ether or amide) and a polyethylene oxide chain and/or an alkyl group containing 1-3 carbon atoms. Non-limiting examples include PEG cocamine, PEG tallow and PEG hydrogenated tallow amine, PEG lauramine, PEG oleamine, PEG palmitamine, PEG soyamine, PEG steramine. Other fatty amines in this class are: dimethyl cocamine, dimethyl hydrogenated tallowamine, dimethyl lauramine, dimethyl myristamine, dimethyl palmitamine, dimethyl soyamine, dimethyl stearamine, dimethyl tallow amine, cocamidopropyl dimethylamine, avocadamidopropyl dimethylamine, behenamidopropyl dimethylamine, isostearamidopropyl dimethylamine, stearamidopropyl dimethylamine, lauramidopropyl dimethylamine, and linoleamidopropyl dimethylamine. Stearamidopropyl dimethylamine and PEG-3 cocamine may be preferred in some instances.

A second class of fatty amines includes those comprised of two or more long chain alkyl groups (as ester, ether or amide) each having an average carbon chain length of 12 or more. Non-limiting examples include: dibehenyl methylamine, dicetyl dimethyl ammonium chloride or bromide, ditallow dimethyl ammonium chloride or bromide, distearyl dimethyl ammonium chloride or bromide, dihydrogenated tallow methylamine, dihydroxyethyl cocamine dioleate, dihydroxyethyl tallowamine dioleate, dihydroxyethyl tallowamine oleate, dilinoleamidopropyl dimethylamine, ditallowamidoethyl hydroxypropylamine, PEG dicocamine, PEG ditallow amine, dihydroxyethyl soyamine dioleate, dihydroxyethyl cocamine dioleate, dihydroxyethyl soyamine dilaurate, PEG ditallow amine. Dihydroxyethyl soyamine dioleate and dicetyl dimethylamonnium chloride are particularly preferred material within this class.

A further group of amines include amido amines or diamines/polyamines, such as PEG tallow aminopropylamine, coco amidoethyl ethylene diamine, lauryl amido propylene diamine. In some cases, the fatty amines are tertiary and quaternary amines that have limited solubility in water at room temperature. In one preferred embodiment, the fatty amine is stearamidopropyl dimethylamine.

Fatty Alcohol(s)

The hair treatment compositions include an amount of fatty alcohol(s) typically in the range of about 0.1 to about 15 wt. %, based on the total weight of the hair treatment composition. For example, the amount of fatty alcohol(s) present in the hair treatment composition may range from about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %; about 0.1 to about 2.5 wt. %, about 0.2 to about 2 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %; about 0.7 to about 15 wt. %, about 0.7 to about 10 wt. %, about 0.7 to about 8 wt. %, about 0.7 to about 6 wt. %, about 0.7 to about 5 wt. %, about 0.7 to about 4 wt. %, about 0.7 to about 3 wt. %; about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %; about 1.5 to about 15 wt. %, about 1.5 to about 10 wt. %, about 1.5 to about 8 wt. %, about 1.5 to about 6 wt. %, about 1.5 to about 5 wt. %, about 1.5 to about 4 wt. %; about 2 to about 15 wt. %, about 2 to about 10 wt. %, about 2 to about 8 wt. %, about 2 to about 6 wt. %, about 2 to about 5 wt. %, about 2 to about 4 wt. %, including all ranges and sub-ranges therebetween, based on the total weight of the hair treatment composition.

The fatty alcohols may be chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, myricyl alcohol and a mixture thereof.

More generally, the fatty alcohols may be liquid at 25° C., 1 atm, or may even be solid. They may even be glycerolated and/or oxyalkylenated, and may include from 8 to 30 carbon atoms. They may be saturated or unsaturated. For example, the fatty alcohols may be chosen from those having from 8 to 30 carbons, e.g., 8 to 25, 8 to 22, 8 to 20, 8 to 18, or 8 to 16 carbons. In some cases, the fatty alcohol has 12 to 30, 12 to 25, 12 to 22, 12 to 20, 12 to 18, or 12 to 16 carbons. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of myristyl alcohol, cetyl alcohol, stearyl alcohol, isostearyl alcohol, oleyl alcohol, isotridecyl alcohol, and a mixture thereof.

The saturated liquid fatty alcohols may be branched. They can optionally comprise, in their structure, at least one aromatic or non-aromatic ring, but are preferably acyclic. Non-limiting examples of liquid saturated fatty alcohols include octyldodecanol, isostearyl alcohol, and 2-hexyldecanol.

The unsaturated liquid fatty alcohols may include in their structure at least one double or triple bond and, in some instances, one or more double bonds. When several double bonds are present, there are preferably 2 or 3 of them and they can be conjugated or non-conjugated. These unsaturated fatty alcohols can be linear or branched. They can optionally include in their structure at least one aromatic or non-aromatic ring but they are preferably acyclic. Among liquid unsaturated fatty alcohols, oleyl alcohol, linoleyl alcohol, linolenyl alcohol and undecylenyl alcohol can be cited.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Non-limiting examples of high melting point fatty compounds include fatty alcohols such as, for example, myristyl alcohol (having a melting point of about 38° C.), cetyl alcohol (having a melting point of about 56° C.), stearyl alcohol (having a melting point of about 58-59° C.), behenyl alcohol (having a melting point of about 71° C.), and mixtures thereof. These compounds are known to have the above melting points. However, they often have lower melting points when supplied, since such supplied products are often mixtures of fatty alcohols having alkyl chain length distribution in which the main alkyl chain is cetyl, stearyl or behenyl group. In the present disclosure, more preferred fatty alcohols are myristyl alcohol, cetyl alcohol, stearyl alcohol and mixtures thereof. In at least one embodiment, the fatty alcohol is chosen from or comprises cetyl alcohol and/or myristyl alcohol.

Emollient(s)

The hair treatment composition may include emollient(s) in an amount that may vary, but typically ranges from about 0.1 to about 15 wt. %, based on the total weight of the hair treatment composition. For example, the amount of fatty amine(s) present in the hair treatment composition may range from about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %; about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %; about 0.7 to about 15 wt. %, about 0.7 to about 10 wt. %, about 0.7 to about 8 wt. %, about 0.7 to about 6 wt. %, about 0.7 to about 5 wt. %, about 0.7 to about 4 wt. %, about 0.7 to about 3 wt. %, about 0.7 to about 2 wt. %; about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %; about 1.5 to about 15 wt. %, about 1.5 to about 10 wt. %, about 1.5 to about 8 wt. %, about 1.5 to about 6 wt. %, about 1.5 to about 5 wt. %, about 1.5 to about 4 wt. %, including all ranges and sub-ranges therebetween, based on the total weight of the hair treatment composition.

Without being limited to any specific theory, emollients, such as isopropyl myristate helps to lower the polarity of the solvent medium, and hence, lowering the crystallization temperature of fatty alcohol.

The emollient may be a polar emollient or a non-polar emollient. As used herein, "polar emollient" means any emollient having at least one polar moiety. The emollient may be one or both of high and medium polarity oil soluble emollients. Non-limiting examples of polar emollients include, but are not limited to, esters, polyol esters, and polyol ethers such as linear or branched chained polyglycerol esters and polyglycerol ethers. For example, the emollient be chosen from or comprise caprylic/capric triglyceride, isopropyl myristate, PPG-3 myristyl ether, isopropyl palmitate, dibutyl adipate, propyleneglycol dicaprylate/dicaprate, cocoglyceride, cetearyl isononanoate, isopropyl myristate, isodecyl neopentanoate, tridecyl neopentanoate, $C_{12-15}$ alkyl benzoate, isopropyl lauroyl sarsosinate, phenethyl benzoate, and mixtures thereof. Other examples of emollients include oil soluble emollients having high or medium polarity moieties.

The emollient may be a non-polar oil soluble emollients. "Non-polar emollient," as used herein, means any emollient possessing no permanent electric moments. Non-limiting examples of non-polar emollients may include, but are not limited to, non-polar hydrocarbon, such as esters, linear or branched, or chained hydrocarbons. For example, the emollients may be chosen form or include paraffins, isoparaffins, mineral oil, silicone oils, dimethicone, isohexadecane, isododecane, diethylhexyl cyclohexane, and mixtures thereof. In some instances, emollient comprises or is chosen from dicaprylyl ether, isododecane, hydrocarbon, dimethicone and mixtures thereof. In other cases, the emollient includes non-silicone oils and dimethicone. In yet further case, the emollient includes dimethicone with one or more additional non-polar emollients.

Preferably, the emollient comprises or is chosen from isopropyl myristate and/or dicaprylyl carbonate.

Thickener(s)

The hair treatment compositions described herein may, optionally, include a thickener. The thickener may be in an amount of about 0.1 wt. % to about 20 wt. %, about 0.1 to about 10 wt. %, about 0.1 wt. % to about 9 wt. %, about 0.2 wt. % to about 9 wt. %, about 0.3 wt. % to about 9 wt. %, about 0.4 wt. % to about 8 wt. %, about 0.5 wt. % to about 5 wt. %, about 1 wt. % to about 5 wt. %, or about 2 wt. % to about 4 wt. %, including ranges and subranges thereof, based on the total weight of the hair treatment composition. Further, the amount of thickener may be from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %, including ranges and subranges thereof, based on the total weight of the hair treatment composition.

The thickener(s) may be chosen from xanthan gum, guar gum, biosaccharide gum, cellulose, acacia seneca gum, sclerotium gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate. Suitable thickeners may be found in U.S. patent application Ser. No. 16/731,654, which is incorporated herein, in its entirety for all purposes.

Many thickeners are water-soluble, and increase the viscosity of water or form an aqueous gel when the hair treatment composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the hair treatment compositions of the instant disclosure. Thickening agents may be referred to as "thickeners" or "viscosity modifying agents." Thickening agents are typically included to increase the viscosity of the hair treatment compositions. Nonetheless, in some instances, certain thickening agents provide additional, surprising benefits to the hair treatment compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw maerial known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Polyquaternium Compounds:

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-Polymers:

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Polyglyceryl Esters:

Non-limiting polyglycerol esters of fatty acids (polygylceryl esters) include those of the following formula:

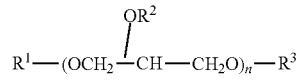

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Gums:

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

The total amount of thickening agents can vary but is typically from about 0.01 to about 20 wt. %, based on the total weight of the hair treatment composition. In some instances, the total amount of thickening agents is about 0.01 to about 15 wt. %, about 0.01 to about 10 wt. %, about 0.01 to about 0.01 to about 8 wt. %, about 0.01 to about 6 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, or about 0.1 to about 5 wt. %, including ranges and sub-ranges therebetween, based on the total weight of the hair treatment composition.

In some instances, the hair treatment compositions include one or more polyacrylate crosspolymers, for example, polyacrylate crosspolymer-6. The total amount of the polyacrylate crosspolymer(s) can vary but may be from about 0.01 to about 10 wt. %, based on the total weight of the hair treatment compositions. In some instances, the total amount of polyacrylate crosspolymers is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the hair treatment composition.

In some instances, the hair treatment compositions include one or more carbomers, which are polymeric materials composed of acrylic acid monomers. The total amount of carbomers may vary but may be from about 0.01 to about 10 wt. %, based on the total weight of the hair treatment compositions. In some instances, the total amount of carbomers is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the hair treatment composition.

In some instances, the hair treatment compositions include acrylamidopropyltrimonium chloride/acrylates copolymer, which is a copolymer of one or more of the monomers formed from the amide of acrylic acid, methacrylic acid and aminopropyltrimethyl-ammonium chloride and one or more monomers of acrylic acid, methacrylic acid or one of their esters. The total amount of acrylamidopropyltrimonium chloride/acrylates copolymer may vary but may be from about 0.01 to about 10 wt. %, based on the total weight of the hair treatment compositions. In some instances, the total amount of acrylamidopropyltrimonium chloride/acrylates copolymer is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the hair treatment composition.

In some instances, the hair treatment compositions include one or more polyquaternium compounds. Non-limiting examples include polyquaternium-10, polyquaternium-11, and polyquaternium-67. The total amount of polyquaternium compounds may vary but may be from about 0.01 to about 10 wt. %, based on the total weight of the hair treatment compositions. In some instances, the total amount of polyquaternium compounds is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the hair treatment composition.

In some instances, the hair treatment compositions include one or more cellulose thickeners (e.g., microcrystalline cellulose, carboxymethylcellulose, hydroxymethylcellulose, and hydroxypropylcellulose). The total amount of cellulose thickeners can vary but may be from about 0.01 to about 10 wt. %, based on the total weight of the hair treatment compositions. In some instances, the total amount of cellulose thickeners is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the hair treatment composition.

In some instances, the hair treatment compositions include polyvinylpyrrolidone (PVP) and/or polyvinylpyrrolidone/vinyl acetate (VP/VA) copolymer. The total amount of PVP and/or VP/VA copolymer can vary but may be from about 0.01 to about 10 wt. %, based on the total weight of the hair treatment compositions. In some instances, the total amount of PVP and/or VP/VA copolymer is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, including ranges and sub-ranges therebetween, based on the total weight of the hair treatment composition.

Water

The hair treatment composition typically includes 10 wt. % or less of water. For example, the amount of water present in the hair treatment composition prior to combination with extraneous water may be 10 wt. % or less, 9 wt. % or less, 8 wt. % or less, 7 wt. % or less, 6 wt. % or less, 5 wt. % or less, 4 wt. % or less, 3 wt. % or less, 2 wt. % or less, 1 wt. % or less, or 0.5 wt. % or less, based on the total weight of the hair treatment composition. In some instances, the water present in the hair treatment composition prior to combination with extraneous water is added to the composition ("added water"). In some instances, the water present in the hair treatment composition prior to combination with extraneous water is not "added water," i.e., it is present in the hair treatment composition as part of a raw material that is included in the hair treatment composition. Although the hair treatment composition may include water prior to the combination of extraneous water, in some embodiments the hair treatment composition is anhydrous or substantially anhydrous.

pH Adjuster(s)

The hair treatment composition may include one or more pH adjusters to increase or decrease the overall pH of the hair treatment composition. For example, one or more acids may be included to decrease the pH of the hair treatment composition. Examples of suitable acids for decreasing the pH of the hair treatment composition include, but are not limited to, citric acid, acetic acid, and the like. The hair treatment composition may include one or more bases, such as sodium hydroxide, potassium hydroxide and the like, to increase the pH of the hair treatment composition. Additional or alternative acids and bases that are suitable for adjusting the pH of the hair treatment composition are readily known to one of ordinary skill in the art.

The hair treatment composition may, desirably, have a pH of less than 10. For example, the hair treatment composition may have a pH of about 2 to less than 10, preferably about 2.5 to about 9 or about 3 to about 8.

The amount of the pH adjuster in the hair treatment composition may be based on the desired pH of the final hair treatment composition and/or product. For example, the total amount of the pH adjuster may range from about 0.05 to about 20 wt. %, based on the total weight of the hair treatment composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the hair treatment composition.

Methods of Treating Hair

Aspects of the instant disclosure also relate to methods for making and using such hair treatment compositions. A method for cleaning hair according to aspects of the disclosure typically includes:

(I) applying a hair treatment composition comprising:
  (a) about 20 wt. % or more of a polyol;
  (b) about 5 to about 50 wt. % of a monoalcohol having a carbon chain of 1 to 10 carbons,
    wherein a weight ratio of the amount of glycol of (a) to the amount of the monoalcohol of (b) is 20:1 to 1:1;
  (c) about 0.1 to about 5 wt. % of a fatty acid;
  (d) about 0.1 to about 15 wt. % of a fatty amine,
    wherein a molar ratio of the amount of the fatty acid of (c) to the amount of the fatty amine of (d) is 0.8:1 to 1.2:1;
  (e) about 0.1 to about 15 wt. % of a fatty alcohol; and
  (f) about 0.1 to about 15 wt. % of an emollient,
    wherein all weight percentages are based on the total weight of the hair treatment composition.
(II) rinsing the hair cleansing composition from the hair.

The methods for treating or cleaning hair according to the disclosure may vary but typically include applying a hair treatment composition as disclosed herein, allowing the hair treatment composition to remain on the hair for a sufficient amount of time, and rinsing the hair treatment compositions from the hair. The hair treatment composition may be applied to the hair in a sequence with other compositions. For example, the hair treatment composition may be applied to the hair before shampooing the hair, after shampooing the hair, before conditioning the hair, and/or after conditioning the hair, etc. The hair treatment compositions, however, are not required to be used in a sequence.

The methods may include applying an amount of the hair treatment composition onto the body, for example, onto one or both hands, onto the hair, onto the face, etc. The body may already be wet or damp with extraneous water or extraneous water can be included after the hair treatment composition has already been applied to the body. The hair treatment composition and the extraneous water may optionally be mixed together on the body to facilitate formation of an opaque emulsion having an increased viscosity. Alternatively, the hair treatment composition and extraneous water may be combined, and optionally mixed, prior to application to the body. For example, the hair treatment composition may be combined in a container, bowl, packaging, bottle, etc., and subsequently applied to the body after formation of the opaque emulsion.

In some instances, the methods include forming the mixed structure and/or an opaque emulsion on the hands and subsequently applying it to the hair. In other instances, the methods include forming the mixed structure and/or opaque emulsion directly on the hair. In yet other instance, the methods include forming an opaque emulsion other the face, or other parts of the body.

The hair treatment compositions and the emulsions formed by combination with water are useful for conditioning and/or managing the hair. The hair treatment compositions and the emulsions formed by combination of water can be applied to the wet or damp hair and may be massaged into the hair, for example, with the hands, and/or spread throughout the hair with a comb or brush. This results in a smoothing and softening of the hair, which reduces frizz, dryness, and unwanted volume.

Another unique aspect of the hair treatment compositions is that they may be used as a leave-on product. The hair treatment compositions can be applied to wet or damp hair and allowed to remain on the hair indefinitely, i.e., the hair treatment composition is not removed or rinsed from the hair prior to styling the hair.

In some cases, the hair treatment compositions are used in conjunction with additional hair-treatment compositions in a routine, for example, during an individual's normal showering/bathing routine. The hair treatment composition may be applied to the hair individually or may be combined with one or more additional compositions. For instance, the hair treatment composition may be mixed with a shampoo (or conditioner) prior to application to the hair. In this case, the mixture of the shampoo (or conditioner) and the hair treatment composition are simultaneously applied to the hair during the cleansing or conditioning process and simultaneously rinsed from the hair. Alternatively, the hair treatment composition may be layered on top of (or lathered into) hair to which a shampoo (or conditioner) has already been applied or vice versa. In this case, the hair treatment composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair treatment composition is also applied to the hair.

When used in conjunction with a shampoo and/or a conditioner, the hair treatment composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair treatment composition of the instant disclosure:shampoo/conditioner, etc.).

The hair treatment compositions of the instant disclosure may be allowed to remain on the hair for a minimum amount of time before being rinsed from the hair, but it is not necessary to allow the hair treatment composition to remain on the hair for an extended period of time. Conveniently, the hair treatment compositions can be applied and allowed to remain on the hair for a period of time that is typical for regular shampooing and/or conditioning. For example, the hair treatment composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

When the hair treatment composition is not being mixed with another composition prior to application to the hair, the hair treatment composition may be applied to the hair immediately after or before the hair is treated with another composition (e.g., a shampoo and/or a conditioner). For example, the hair treatment compositions may be applied to the hair within about a few seconds or 1, 2, 5, 10, or 20 minutes before or after a shampoo and/or a conditioner is applied to the hair.

The hair treatment compositions of the instant disclosure are unique in their ability to provide hair with improved smoothness, lightness, and shine. Accordingly, the instant disclosure relates to methods for treating hair, for example, for improving the manageability of hair and/or for imparting smoothness. More specifically, the hair treatment compositions may be used in methods for conditioning the hair, improving ease of combability and detangling, and providing smoothness.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair cleansing compositions of the instant disclosure can be free or essentially free of all components and elements positively recited throughout the instant disclosure. In some instances, the hair cleansing compositions of the present disclosure may be substantially free of non-incidental amounts of the ingredient(s) or compound(s) described herein. A non-incidental amount of an ingredient or compound is the amount of that ingredient or compound that is added into the hair cleansing composition by itself. For example, a hair cleansing composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair cleansing composition includes both components (or the composition includes more than two components that overlap), an overlapping compound does not represent more than one component. For example, certain compounds may be characterized as both an emulsifier and a surfactant. If a particular hair composition includes both an emulsifier and a surfactant, the compounds that may be characterized as both an emulsifier and a surfactant will serve only as either the emulsifier or the surfactant—not both.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations. Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

EMBODIMENTS OF THE DISCLOSURE

In certain embodiments, the hair treatment compositions of the instant disclosure include:
about 20 wt. % or more, preferably about 20 to about 87 wt. %, more preferably about 20 to about 80 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;
about 5 wt. % to about 50 wt. %, preferably about 5 to about 40 wt. %, more preferably about 10 to about 30 wt. %, of a monoalcohol having 1 to 10 carbons including, e.g., ethanol, propanol, butanol, pentanol, hexanol, isopropyl alcohol, cycohexanol, isobutyl alcohol, 2-methyl-2-butanol (2-methylbutan-2-ol), and a mixture thereof,
wherein a weight ratio of the amount of polyol of (a) to the amount of the monoalcohol of (b) is 20:1 to 1:1, preferably 10:1 to 1:1;
about 0.1 to about 5 wt. %, preferably about 0.1 to about 4 wt. %, more preferably about 0.2 to about 3 wt. % of a fatty acid, even more preferably about 0.5 to about 2 wt. %, wherein the fatty acid is chosen from lauric acid, palmitic acid, stearic acid, behenic acid, arichidonic acid, oleic acid, isostearic acid, sebacic acid, and a mixture thereof, and preferably chosen from lauric acid, palmitic acid, stearic acid, behenic acid, oleic acid, isostearic acid, and a mixture thereof;
about 0.1 to about 15 wt. %, preferably about 0.1 to about 8 wt. %, more preferably about 0.1 to about 5 wt. %, even more preferably about 0.2 to about 3 wt. %, of a fatty amine, such as an alkylamines, an alkylamidoamines, or a mixture thereof, wherein a molar ratio of the amount of the fatty acid of (c) to the amount of the fatty amine of (d) is 0.8:1 to 1.2:1, preferably 0.85:1 to 1.15:1;
about 0.1 to about 15 wt. %, preferably about 1 to about 10 wt. %, more preferably about 1.5 to about 8 wt. %, even more preferably about 1.5 to about 4 wt. %, of a fatty alcohol, such as those chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, myricyl alcohol and a mixture thereof; and
about 0.1 to about 15 wt. %, preferably about 0.5 to about 10 wt. %, more preferably about 1 to about 8 wt. %, even more preferably about 1 to about 5 wt. %, of an emollient, such as isopropyl myristate,
wherein all weight percentages are based on the total weight of the hair treatment composition.

In further embodiments, the hair treatment compositions of the instant disclosure include:
 about 60 to about 87 wt. %, preferably about 60 to about 80 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;
 about 10 to about 30 wt. %, preferably about 15 to about 30 wt. %, more preferably about 15 to about 25 wt. %, of a monoalcohol comprising chosen from ethanol, propanol, butanol, pentanol, an isomer thereof, or a combination thereof,
wherein a weight ratio of the amount of polyol of (a) to the amount of the monoalcohol of (b) is 20:1 to 1:1, preferably 10:1 to 1:1;
 about 0.1 to about 5 wt. %, preferably about 0.1 to about 4 wt. %, more preferably about 0.2 to about 3 wt. %, even more preferably about 0.5 to about 2 wt. %, of a fatty acid, such as palmitic acid;
 about 0.1 to about 15 wt. %, preferably about 0.1 to about 8 wt. %, more preferably about 0.1 to about 5 wt. %, even more preferably about 0.2 to about 3 wt. %, of a fatty amine, such as an alkylamine, an alkylamidoamine, or a mixture thereof,
wherein a molar ratio of the amount of the fatty acid of (c) to the amount of the fatty amine of (d) is 0.8:1 to 1.2:1, preferably 0.85:1 to 1.15:1;
 about 0.1 to about 15 wt. %, preferably about 0.1 to about 10 wt. %, more preferably about 0.1 to about 8 wt. %, even more preferably about 1.5 to about 4 wt. %, of a fatty alcohol, such as cetyl alcohol; and
 about 0.1 to about 15 wt. %, preferably about 0.5 to about 10 wt. %, more preferably about 1 to about 8 wt. %, even more preferably about 1 to about 5 wt. %, of an emollient, such as isopropyl myristate, wherein all weight percentages are based on the total weight of the hair treatment composition.

In additional embodiments, a method is provided for treating hair including:
 (I) applying a hair treatment composition comprising:
  about 20 wt. % or more, preferably about 20 to about 87 wt. %, more preferably about 20 to about 80 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;
  about 5 wt. % to about 50 wt. %, preferably about 5 to about 40 wt. %, more preferably about 10 to about 30 wt. %, of a monoalcohol having 1 to 10 carbons including, e.g., ethanol, propanol, butanol, pentanol, hexanol, isopropyl alcohol, cycohexanol, isobutyl alcohol, 2-methyl-2-butanol (2-methylbutan-2-ol), and a mixture thereof,
wherein a weight ratio of the amount of polyol of (a) to the amount of the monoalcohol of (b) is 20:1 to 1:1, preferably 10:1 to 1:1;
  about 0.1 to about 5 wt. %, preferably about 0.1 to about 4 wt. %, more preferably about 0.2 to about 3 wt. %, even more preferably about 0.5 to about 2 wt. %, of a fatty acid, wherein the fatty acid is chosen from lauric acid, palmitic acid, stearic acid, behenic acid, arichidonic acid, oleic acid, isostearic acid, sebacic acid, and a mixture thereof, and preferably chosen from lauric acid, palmitic acid, stearic acid, behenic acid, oleic acid, isostearic acid, and a mixture thereof;
  about 0.1 to about 15 wt. %, preferably about 0.1 to about 8 wt. %, more preferably about 0.1 to about 5 wt. %, even more preferably about 0.2 to about 3 wt. %, of a fatty amine, such as an alkylamines, an alkylamidoamines, or a mixture thereof,
wherein a molar ratio of the amount of the fatty acid of (c) to the amount of the fatty amine of (d) is 0.8:1 to 1.2:1, preferably 0.85:1 to 1.15:1;
  about 0.1 to about 15 wt. %, preferably about 1 to about 10 wt. %, more preferably about 1.5 to about 8 wt. %, even more preferably about 1.5 to about 4 wt. %, of a fatty alcohol, such as those chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, myricyl alcohol and a mixture thereof; and
  about 0.1 to about 15 wt. %, preferably about 0.5 to about 10 wt. %, more preferably about 1 to about 8 wt. %, even more preferably about 1 to about 5 wt. %, of an emollient, such as isopropyl myristate,
wherein all weight percentages are based on the total weight of the hair treatment composition.
 (II) rinsing the hair cleansing composition from the hair.

EXAMPLES

Implementation of the present disclosure is provided by way of the following examples. The following examples serve to elucidate aspects of the technology without being limiting in nature.

Example 1

Three hair treatment compositions (Example Compositions A-C) were prepared in accordance with aspects of the disclosure. The formulations for Example Compositions A-C and comparative hair treatments (Comparative Compositions D-F) are shown in Table 1, provided below.

TABLE 1

| | | INCI | Ex. A | Ex. B | Ex. C | Comp. D | Comp. E | Comp. F |
|---|---|---|---|---|---|---|---|---|
| (a) | Polyol | PROPYLENE GLYCOL | 72.3 | 74.3 | 73.65 | 77.3 | 73 | 40 |
| (b) | MONOALCOHOL | ETHANOL | 20 | 20 | 20 | 20 | 20 | 20 |
| | | ISOPROPYL ALCOHOL | | | | | 0.1 | |
| Weight ratio of polyol of (a) to monoalcohol of (b) of 20:1 to 1:1 | | | 3.62 | 3.72 | 3.68 | 3.9 | 3.6 | 2 |
| (c) | Fatty acid | PALMITIC ACID | 0.7 | 0.7 | 0.7 | 0.7 | | |

TABLE 1-continued

| | | INCI | Ex. A | Ex. B | Ex. C | Comp. D | Comp. E | Comp. F |
|---|---|---|---|---|---|---|---|---|
| (d) | Fatty amine | STEARAMIDOPROPYL DIMETHYLAMINE | 1 | 1 | 1 | 1 | | |
| | Molar ratio of fatty acid of (c) to fatty amine of (d) of 1:1 to 1:40 | | 1:1 | 1:1 | 1:1 | 1:1 | | |
| (e) | Fatty Alcohol | CETYL ALCOHOL | 2 | 2 | 0.65 | | | 7 |
| | | MYRISTYL ALCOHOL | | | | | 2 | 9 |
| (f) | Emollient | ISOPROPYL MYRISTATE | 3 | 1 | 3 | | | |
| | | DICAPRYLYL CARBONATE | | | | | 0.9 | |
| | | SILICONE | | | | | | 1.3 |
| | | ESTER OIL | | | | | | 9.8 |
| | | DI-C12-13 ALKYL MALATE | | | | | | 1.0 |
| | Cationic Surfactant | CETRIMONIUM CHLORIDE AND/OR BEHENTRIMONIUM CHLORIDE AND/OR BEHENTRIMONIUM METHOSULFATE | | | | | 1.2 | 4.5 |
| | | | | | | | 0.6 | |
| | | | | | | | | 2.0 |
| | pH Adjuster | TARTARIC ACID | | | | | | 0.1 |
| | Fragrance | FRAGRANCE | 1 | 1 | 1 | 1 | 1 | 1 |
| | Preservative | TOCOPHEROL | | | | | <0.01 | |
| | Water | WATER | | | | | QS 100 | QS 100 |

Example 2

Exemplary Composition A was evaluated in comparison to Comparative Composition E. Expert evaluators applied Exemplary Composition A and Comparative Composition E to 10 individuals for this evaluation. Specifically, the expert evaluators applied Exemplary Composition A to a first half of an individual's head of hair and applied Comparative Composition E to the second half of the individual's head of hair.

During application, Exemplary Composition A exhibited noticeably more suppleness than Comparative Composition E. Exemplary Composition A also exhibited slightly higher levels of absorption than Comparative Composition E. Exemplary Composition A exhibited slightly lower levels of on-surface effect, stickiness, and distribution to the ends. However, the slightly lower levels of the foregoing characteristics may be unnoticeable to untrained users (e.g., typical consumers).

Exemplary Composition A exhibited slightly lower wet detangling, wet hair combing, wet coating, ease of shaping with a brush, and ease of passing fingers through the hair than Comparative Composition E during the wet stage. Similarly, the slightly lower effects of Exemplary Composition A may be unnoticeable to untrained users (e.g., typical consumers).

During the dry stage, Exemplary Composition A exhibited parity in evaluated characteristics with Comparative Composition E. Overall, Comparative Composition E may have felt slightly smoother than Exemplary Composition A after rinsing, although Exemplary Composition A felt smooth as well. The slight difference in smoothness in Comparative Composition E as compared to Exemplary Composition A may be unnoticeable to untrained users (e.g., typical consumers). Accordingly, the only difference between Exemplary Composition A and Comparative Composition E that is likely to be noticed by untrained users is the increased suppleness during the application of Exemplary Composition A.

Example 3

Exemplary Composition A and Comparative Composition F were evaluated under a microscope. As shown in FIGURE, Exemplary Composition A exhibited a mixed structure having round crystals, while Comparative Composition F exhibited only a lamellar phase.

What is claimed is:
1. A hair treatment composition consisting of:
   (a) about 60 to about 87 wt. % of a polyol chosen from ethylene glycol, propylene glycol, butylene glycol, hexylene glycol, glycerin, diglycerin, diethylene glycol, dipropylene glycol, and mixtures thereof;
   (b) about 10 wt. % to about 30 wt. % of a monoalcohol chosen from ethanol, propanol, butanol, pentanol, an isomer thereof, or a combination thereof,
      wherein a weight ratio of the amount of the polyol of (a) to the amount of the monoalcohol of (b) is 5:1 to 2:1;
   (c) about 0.1 to about 5 wt. % of a fatty acid;
   (d) about 0.1 to about 5 wt. % of a fatty amine,
      wherein a molar ratio of the amount of the fatty acid of (c) to the amount of the fatty amine of (d) is 0.8:1 to 1.2:1;
   (e) about 0.1 to about 15 wt. % of a fatty alcohol;
   (f) about 0.1 to about 15 wt. % of one or more emollients; and
   (g) optionally, one or more fragrances, preservatives, and pH adjusters;
      wherein the hair treatment composition comprises less than 6 wt. % of water, and all weight percentages are based on the total weight of the hair treatment composition.
2. The hair treatment composition of claim 1, wherein one of the one or more emollients is isopropyl myristate.
3. The hair treatment composition of claim 1, wherein the polyol is propylene glycol.
4. The hair treatment composition of claim 1, wherein the monoalcohol is ethanol.

5. The hair treatment composition of claim 1, wherein the molar ratio of the amount of the fatty acid of (c) to the amount of the fatty amine of (d) is 0.85:1 to 1.15:1.

6. The hair treatment composition of claim 1, wherein the molar ratio of the amount of the fatty acid of (c) to the amount of the fatty amine of (d) is 0.9:1 to 1.1:1.

7. The hair treatment composition of claim 1, wherein the fatty acid is chosen from lauric acid, myristic acid, palmitic acid, stearic acid, or a mixture thereof.

8. The hair treatment composition of claim 1, wherein the fatty amine is chosen from an alkylamine, an alkylamidoamine, or a mixture thereof.

9. The hair treatment composition of claim 1, wherein the fatty alcohol has a carbon chain of 12 to 18 carbons.

10. The hair treatment composition of claim 1, wherein the carbon chain of the fatty amine has a length that is within 4 carbon atoms of the length of the carbon chain of the fatty acid.

11. A method of treating hair comprising applying a hair treatment composition according to claim 1.

* * * * *